United States Patent

Hallas et al.

[11] 4,063,014
[45] Dec. 13, 1977

[54] 4''-O-SULFONYL ERYTHROMYCIN-9-O-OXIME DERIVATIVES

[75] Inventors: Robert Hallas; Jerry Roy Martin; John Soloman Tadanier, all of Waukegan, Ill.

[73] Assignee: Abbott Laboratories, North Chicago, Ill.

[21] Appl. No.: 586,127

[22] Filed: June 12, 1975

[51] Int. Cl.² .................... C07H 17/08; A61K 31/70
[52] U.S. Cl. .......................................... 536/9; 424/180
[58] Field of Search .......................... 260/210 E; 536/9

[56] References Cited
U.S. PATENT DOCUMENTS

| 3,836,819 | 9/1974 | Hallas et al. | 260/210 E |
| 3,869,445 | 3/1975 | Hallas et al. | 260/210 E |

Primary Examiner—Henry R. Jiles
Assistant Examiner—Cary Owens
Attorney, Agent, or Firm—Paul D. Burgauer; Robert L. Niblack

[57] ABSTRACT

A 4''-O-sulfonyl erythromycin derivative of the following structural formula:

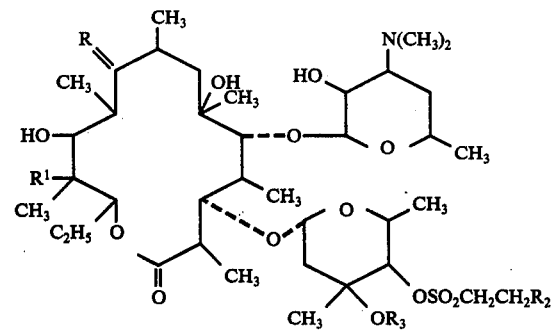

where R is selected from the group consisting of oxygen, oxime, and substituted oxime, $R_1$ is hydrogen or hydroxy and $R_2$ is selected from the group consisting of phthalimide, substituted amides, benzamides, substituted benzamides, sulfonamides, substituted sulfonamides, amines, substituted amines, phenylurea, substituted phenylurea, phenylthiourea, substituted phenylthiourea, thiophenol and substituted thiophenol, phenoxides and substituted phenoxides and $R_3$ is hydrogen or methyl. The present sulfonyl derivatives of erythromycin A, B and C are useful as antibiotics.

6 Claims, No Drawings

4"-O-SULFONYL ERYTHROMYCIN-9-O-OXIME DERIVATIVES

DESCRIPTION OF THE INVENTION

This invention relates to antibiotic derivatives of erythromycin A and B, and more particularly to 4"-O-sulfonyl erythromycin A and B 9-O-oxime derivatives. The novel compounds of this invention have the following structural formula:

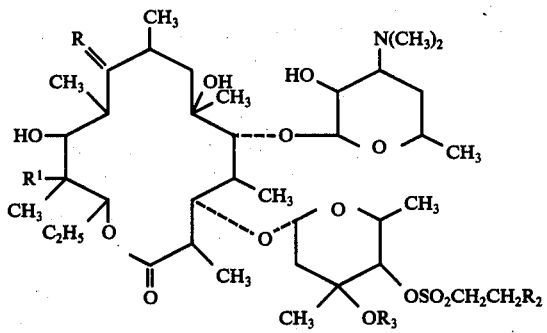

where R is selected from the group consisting of oxygen, oxime, and substituted oxime, $R_1$ is hydrogen or hydroxy and $R_2$ is selected from the group consisting of phthalimide, substituted amides, benzamides, substituted benzamides, sulfonamides, substituted sulfonamides, amines, substituted amines, phenylurea, substituted phenylurea, phenylthiourea, substituted phenylthiourea, thiophenol and substituted thiophenol, phenoxides and substituted phenoxides and $R_3$ is hydrogen or methyl. The present sulfonyl derivatives of erythromycin A, B and C are useful as antibiotics.

Erythromycin is produced in three forms denoted A, B and C by cultivating a strain of *Streptomyces erythreus* in a suitable nutrient medium as is taught in U.S. Pat. No. 2,653,899, Bunch, et al. The structure of erythromycin is represented by the following formula:

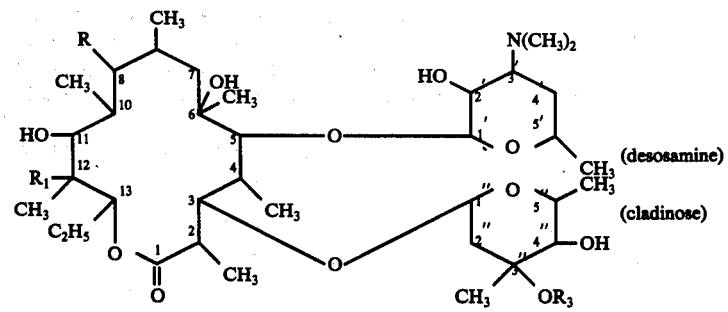

In this formula, when $R_3$ is methyl and $R_1$ is hydroxyl, the structure illustrated is erythromycin A. When $R_3$ is methyl and $R_1$ is hydrogen, the structure of erythromycin B is illustrated. When $R_3$ is hydrogen and $R_1$ is hydroxyl, the structure of erythromycin C is illustrated. The term "erythromycin" when used herein without modification is meant to embrace all three forms, that is, erythromycin A, B and C.

Erythromycin, as will be noted from the formula, comprises three cyclic fragments. These fragments are referred to respectively as cladinose, desosamine and erythronolide. The positions on the cladinose ring are indicated by double primed numbers; the positions on the desosamine ring by single primed numbers; while positions on the erythronolide ring are indicated by unprimed numbers.

The starting materials in preparing the compounds of the invention may be prepared via a diverse number of synthetic routes. However, the best procedure is to first form the 9-O-oxime derivative or erythromycin according to the techniques outlined in U.S. Pat. No. 3,681,326. By the methods enumerated there a number oxime derivatives may be prepared to produce oxime erythromycins.

After the oxime derivative is prepared, thereafter said derivative is reacted to place a vinyl group on the 4"-position of the erythromycin molecule. The 4"-O-vinyl-sulfonyl erythromycin-9-O-oxime derivatives are best prepared by following the procedures outlined in U.S. Pat. No. 3,836,519.

After the vinyl-oxime erythromycin derivatives are made, the compounds of this invention are prepared by reacting said derivative with a reactant having a labile hydrogen whereby addition across the erythromycin double bond (4" vinyl group) is effected.

The following examples more clearly illustrate the invention.

EXAMPLE I
4"-O-(β-Phthalimidoethyl)Sulfonyl Erythromycin B

To a cooling solution of 32.3 g. (0.045 M.) of Erythromycin B in 400 ml of pyridine, 23.8 g. (0.092 M.) of β-Phthalimidoethane-sulfonyl chloride was added in one portion. After the addition, the reaction was allowed to stir in the ice bath for two hours. After this period of time, the reaction was poured into 3 liters of 5% $NaHCO_3$ solution and extracted three times with 300 ml portions of chloroform. The extracts were combined, dried of $MgSO_4$, filtered and concentrated to leave 43.4 grams of product. This material was recrystallized from Ethyl Acetate to obtain 27.8 grams of pure material. M.P. = 135°–138°.

Analysis: Theory: C:59.10; H:7.81; N:2.93; Found: C:58.51; H:7.82; N:2.97

EXAMPLE II
4"-O-(β-Phthalimidoethyl)Sulfonyl Erythromycin A-9-O Benzyloxime

The compound was prepared the same as described in Example I. From 8.4 g (0.01 M) of Erythromycin A-9-O Benzyloxime to obtain 10.94 grams of crude material. This material was purified by column chromatography to obtain an analytically pure material.

Analysis: Theory: C:60.26; H:7.59; N:3.90; Found: C:59.94; H:7.59; N:3.79

EXAMPLE III
4"-O-(β-Aminoethyl)Sulfonyl Erythromycin B

To a solution of 27.8 g (0.029 M) of 4"-O-(β-Phthalimidoethyl)sulfonyl Erythromycin B in 400 ml of dioxane, 30 ml of 85% Hydiazine Hydiate was added, followed by 30 ml of $H_2O$. This solution was allowed to stir at room temperature for 2 days. After this period of time, the solution was poured into 2 liters of 5% $NaHCO_3$ solution and extracted three times with 300 ml portions of $CHCl_3$. The extracts were combined and washed with 500 ml of cold $H_2O$. The organic layer was dried over MgSO₄, filtered and concentrated to leave 22.3 grams of desired product. The crude material was purified by recrystallization from ether. M.P. = 198°–200°(dec.).

The analysis agreed with the desired product.

EXAMPLE IV

4''-O-(β-Aminoethyl)Sulfonyl Erythromycin A-9-O Benzyloxime

The compound was prepared the same as described in Example 3. From 4.25 g (3.95 mM) of 4''-O-(β-Phthalimidoethyl) sulfonyl Erythromycin A-9-O Benzyloxime to obtain 3.83 grams of desired product. This material was purified by recrystallization from ether. M.P. = 168°–169°.

The analysis agreed with the desired product.

EXAMPLE V

4''-O-[β-(3-Phenylthioureido)-1-Ethyl]sulfonyl Erythromycin-A-9-O-Methyloxime

To a solution of 1.74 g (2.00 mM) of 4''-O-(β-Aminoethyl)sulfonyl Erythromycin A-9-O-Methyloxime in 30 ml of methylene chloride, 300 mg (2.20 mM) of Phenylisothiocyanate was added and was magnetically stirred at room temperature overnight. After this period of time, the solution was concentrated to leave 1.95 grams of crude material. This crude material was purified by column chromatography to obtain an analytically pure sample. The analysis agreed with the desired product.

EXAMPLE VI

4''-O-[β-(3-Phenylureido)-Ethyl]sulfonyl Erythromycin A-9-O-Methyloxime

This material was prepared the same as described in Example V. From 1.74 g (2.00 mM) of 4''-O-(β-Aminoethyl)sulfonyl Erythromycin A-9-O-Methyloxime to obtain 2.03 grams of desired product. This material was purified by column chromatography to obtain an analytically pure sample.

Analysis: Theory: C:57.06; H:8.15; N:5.66; Found: C:56.64; H:8.49; N:5.26

EXAMPLE VII

4''-O-[β-3-(p-Dimethylaminophenylthioureido)-1-Ethyl]sulfonyl Erythromycin A-9-O-Methyloxime The compound was prepared the same as described in Example V. From 2.96 g (3.40 mM) of 4''-O-(β-Aminoethyl)sulfonyl Erythromycin A-9-O-Methyloxime to obtain 3.70 grams of desired product. This material was purified by column chromatography to obtain an analytically pure sample.

Analysis: Theory: C:56.13; H:8.17; N:6.68; Found: C:56.84; H:8.26; N:6.39

EXAMPLE VIII

4''-O-[β-3-(p-Methoxyphenylureido)-1-Ethyl]sulfonyl Erythromycin A-9-O-Methyloxime The compound was prepared the same as described in Example V. From 2.61 grams (3.00 mM) of 4''-O-(β-Aminoethyl) sulfonyl Erythromycin A-9-O Methyloxime to obtain 3.07 grams of crude material. This material was purified by column chromatography to obtain an analytically pure sample.

Analysis: Theory: C:56.56; H:8.11; N:5.50; Found: C:56.72; H:8.22; N:5.28

EXAMPLE IX

4''-O-[β-3-(p-Chlorophenylureido)-1-Ethyl]sulfonyl Erythromycin A-9-O-Methyloxime This compound was prepared the same as described in Example V. From 2.61 g (3.00 mM) of 4''-O-(β-Aminoethyl)sulfonyl Erythromycin A-9-O-Methyloxime to obtain 3.01 grams of desired product. This material was purified by column chromatography to obtain an analytically pure sample.

Analysis: Theory: C:55.14; H:7.78; N:5.47; Found: C:55.28; H:7.90; N:5.47

EXAMPLE X

4''-O-[β-3-(p-Nitrophenylthiouredio)1-Ethyl]Sulfonyl Erythromycin A-9-O-Methyloxime This compound was prepared the same as described in Example V. From 4.30 g (5.00 mM) of 4''-O-(β-Aminoethyl)sulfonyl Erythromycin A-9-O-Methyloxime to obtain 5.66 grams of crude material. This material was purified by column chromatography to obtain an analytically pure sample.

Analysis: Theory: C:53.75; H:7.58; N:6.67; Found: C:54.13; H:7.85; N:6.44

EXAMPLE XI

4''-O-(β-Acetamidoethyl)Sulfonyl Erythromycin A-9-O-Methyloxime

To a solution of 3.40 g (4.00 mM) of 4''-O-(β-Aminoethyl)sulfonyl Erythromycin A-9-O-Methyloxime in 50 ml of pyridine, 800 mg (4.40 mM) of p-Nitrophenylacetate was added in one portion. After this addition, the solution was allowed to stir at room temperature overnight. After being stirred overnight, the solution was poured into 400 ml of 10% K₂CO₃ solution and extracted twice with 300 ml portions of chloroform. The extracts were combined and washed twice with 200 portions of 10% K₂CO₃ solution. The layers were separated, dried over MgSO₄, filtered and concentrated to leave 3.51 grams of material. This material was purified by column chromatography to obtain an analytically pure sample.

Analysis: C:55.30; H:8.31; N:4.61; Found: C:54.87; H:8.65; N:4.57

EXAMPLE XII

4''-O-[β-(N-Carbobenzyloxyglycyl)Amidoethyl]Sulfonyl Erythromycin A-9-O-Methyloxime This compound was prepared the same as described in Example XI. From 3.40 g (4.00 mM) of 4''-O-(β-Aminoethyl)sulfonyl Erythromycin A-9-O-Methyloxime to obtain 4.20 grams of desired product. This product was purified by column chromatography to obtain an analytically pure sample.

Analysis: Theory: C:56.68; H:7.98; N:5.28; Found: C:56.47; H:8.00; N:5.06

EXAMPLE XIII

4''-O-(β-Cyclopropylamidoethyl)Sulfonyl Erythromycin A-9-O-Methyloxime

The compound was prepared the same as described in Example XI. From 2.60 g (3.00 mM) of 4''-O-(β-Aminoethyl)sulfonyl Erythromycin A-9-O-Methyloxime to obtain 2.83 grams of desired product. This material was purified by column chromatography to obtain an analytically pure sample.

Analysis: Theory: C:56.33; H:8.49; N:4.48; Found: C:56.64; H:8.70; N:4.43

EXAMPLE XIV

4"-O[β-(p-Nitrobenzamido)ethyl]Sulfonyl Erythromycin B-9-O-Methyloxime

This compound was prepared the same as described in Example XI. From 4.30 g (5.00 mM) of 4"-O-(β-Aminoethyl)Sulfonyl Erythromycin B-9-O-Methyloxome to obtain 4.96 grams of desired product. This material was purified by column chromatography to obtain an analytically pure sample.

Analysis: Theory: C:56.27; H:7.84; N:5.59; Found: C:56.31; H:7.95; N:5.37

EXAMPLE XV

4"-O-[β-(p-Nitrobenzamido)ethyl]Sulfonyl Erythromycin A-9-O-Methyloxime

This compound was prepared the same as described in Example XI. From 3.40 g (4.00 mM) of 4"-O-(β-Aminoethyl)sulfonyl Erythromycin A-9-O-Methyloxime to obtain 4.23 grams of desired product. This material was purified by recrystallization from isopropyl alcohol to obtain analytically pure sample. M.P = 198°–199°.

Analysis: Theory: C:55.38; H:7.71; N:5.50; Found: C:55.22; H:8.04; N:5.45

EXAMPLE XVI

4"-O-[β-(p-Aminobenzamido)Ethyl]Sulfonyl Erythromycin A-9-O-Methyloxime

To 1.0 g of 5% Palladium on carbon in 50 ml of ethanol (prehydrogenated) was added 1.75 g. (1.63 mM) of 4"-O-[β-(p-Nitrobenzamido)Ethyl]Sulfonyl Erythromycin A-9-O-Methyloxime in 100 ml of methanol and hydrogenated under 3 atmospheres of hydrogen for 24 hours. After this period of time, the catalyst was removed by filtration and washed well with fresh ethanol. The filtrate was concentrated to leave 1.58 grams of material. This material was dissolved in 400 ml of chloroform and washed with 200 ml of 5% NaHCO₃ solution. The layers were separated and the organic layer was dried over MgSO₄, filtered and concentrated to leave a glass. This material was purified by column chromatography to obtain an analytically pure sample.

Analysis: Theory: C:57.06; H:8.15; N:5.67; Found: C:57.17; H:8.32; N:5.43

EXAMPLE XVII

4"-O-[β-(p-Nitrobenzenesulfonamido)Ethyl]Sulfonyl Erythromycin A-9-O-Methyloxime This compound was prepared the same as described in Example I. From 4.30 g (5.00 mM) of 4"-O-(β-Aminoethyl)Sulfonyl Erythromycin A-9-O-Methyloxime to obtain 5.04 grams of desired product. This material was recrystallized from acetone to obtain an analytically pure sample. M.P = 229°–232°.

Analysis: Theory: C:52.55; H:7.48; N:4.95; Found: C:52.75; H:7.55; N:5.19

EXAMPLE XVIII

4"-O-[β-(p-Aminobenzenesulfonamido)Ethyl]Sulfonyl Erythromycin A-9-O-Methyloxime This compound was prepared the same as described in Example XVI. From 2.32 g. (2.20 mM) of 4"-O-[β-(p-Nitrobenzenesulfonamido) Ethyl]sulfonyl Erythromycin A-9-O-Methyloxime to obtain 2.15 grams of desired material. This material was purified by column chromatography to obtain an analytically pure sample.

EXAMPLE XIX

4"-O-(β-Phenoxyethyl)Sulfonyl Erythromycin B-9-O-Oxime

To a solution of 4.1 g (4.55 mM) of 4"-O-(β-Phenoxyethyl)Sulfonyl Erythromycin B in 30 ml of pyridine, 1.4 g (0.02 M) of Hydroxylamine HCl was added. After all of the hydroxylamine HCl had dissolved, the solution was allowed to stand at room temperature for 7 days. After this period of time, the solution was poured into 250 ml of 5% NaHCO₃ solution and extracted twice with 300 ml portion of chloroform. The organic layer was dried over MgSO₄, filtered and concentrated to leave 4.1 grams of material. This material was recrystallized from isopropyl alcohol to obtain an analytically pure sample. M.P = 125°–128°.

Analysis: Theory: C:58.93; H:8.35; N:3.06; Found: C:58.49; H:8.61; N:2.98

EXAMPLE XX

4"-O-[β-(p-Chlorophenylthio)Ethyl]Sulfonyl Erythromycin B-9-O-Oxime

The compound was prepared the same as described in Example XIX. From 4.90 grams (5.15 mM) of 4"-O-[β-(p-Chlorophenylthio)ethyl]sulfonyl Erythromycin B to obtain 4.89 grams of desired product. This material was recrystallized from 12A alcohol to obtain 3.11 grams of pure material. M.P = 215°–217°.

Analysis: Theory: C:55.85; H:7.81; N:2.90; Found: C:55.77; H:8.07; N:2.89

EXAMPLE XXI

4"-O-(β-Phenylthioethyl)Sulfonyl Erythromycin A-9-O-Oxime

The compound was prepared the same as described in Example XIX. From 4.50 grams (4.82 mM) of 4"-O-(β-Phenylthioethyl)sulfonyl Erythromycin A to obtain 4.56 grams of crude material. This material was recrystallized from 12A alcohol to obtain an analytically pure material. M.P = 225°–227°.

Analysis: Theory: C:55.76; H:8.60; N:4.54; Found: C:55.73; H:8.90; N:4.42

EXAMPLE XXII

4"-O-(β-Thiomorpholinoethyl)Sulfonyl Erythromycin B-9-O-Oxime

The compound was prepared the same as described in Example XIX. From 3.90 g (4.25 mM) of 4"-O-(β-Thiomorpholinoethyl)sulfonyl Erythromycin B to obtain 3.54 grams of crude material. The material was recrystallized from 12A alcohol to obtain an analytically pure sample. M.P = 232°–233°.

Analysis: Theory: C:55.76; H:8.60; N:4.54; Found: C:55.73; H:8.90; N:4.42

EXAMPLE XXIII

4"-O-(β-Dimethylaminoethyl)Sulfonyl Erythromycin A-9-O-Oxime

The compound was prepared the same as described in Example XIX. From 3.03 grams (3.49 mM) of 4"-O-(β-Dimethylaminoethyl)sulfonyl Erythromycin A to obtain 3.10 grams of desired product. This material was recrystallized from ether to obtain an analytically pure sample. M.P = 154°–157°.

Analysis: Theory: C:55.70; H:8.78; N:4.75; Found: C:55.46; H:9.00; N:4.66

A wide variety of organisms were used to test the in vitro activity of the compounds here. These are as follows:

I

Agar Dilution Test

1. *Staphylococcus aureus* 9144
2. *Staphylococcus aureus* Smith
3. *Staphylococcus aureus* Smith ER
4. *Staphylococcus aureus* Quinones
5. *Staphylococcus aureus* Wise 155
6. *Streptococcus faecalis* 10541
7. *Escherichia coli* Juhl
8. *Klebsiella, pneumoniae* 10031
9. *Proteus vulgaris* Abbott JJ
10. *Proteus mirabilis* Finland No. 9
11. *Salmonella typhimurium* Ed No. 9
12. *Shigella sonnet* 9290
13. *Pseudomonas aeruginosa* BMH No. 10
14. *Streptococcus pyogenes* Roper
15. *Streptococcus pyogenes* Scott
16. *Haemophilus influenzae* 9334
17. *Haemophilus influenzae* Brimm CSF
18. *Haemophilus influenzae* Illinois
19. *Haemophilus influenzae* Paterson
20. *Haemophilus influenzae* Shemwell
21. *Haemophilus influenzae* Terry

II

1. *Myco. gallisepticum* S6
2. *Myco. granularum* 19168
3. *Myco. hyorhinis* 17981
4. *Myco. pneumoniae* FH
5. *Trichomonas vaginalis* ClM1
6. *Crithidia fasciculata*

III

Broth Dilution Test

1. *Staphylococcus aureus* Quinones
2. *Staphylococcus aureus* Wise 155
3. *Staphylococcus aureus* Smith
4. *Streptococcus pyogenes* Roper
5. *Streptococcus pyogenes* Scott

IV-I

Induced Erythromycin Strains

1. *Staphylococcus aureus* 209 PER
2. *Staphylococcus aureus* Smith ER

IV-II

Natural Erythromycin Resistant Strains

1. *Staphylococcus aureus* MIH No. 7
2. *Staphylococcus aureus* Wise J.66
3. *Staphylococcus aureus* Wise J.348
4. *Staphylococcus aureus* Wise J.419
5. *Staphylococcus aureus* Wise J.645
6. *Diplococcus pneumoniae* Dixon 23

A = Erythromycin A
B = Erythromycin B
P = Product

In vitro results are as follows:

| I | A | B | P |
|---|---|---|---|
| 1 | .39 | .39 | .78 |
| 2 | .20 | .39 | .78 |
| 3 | >100 | >100 | >100 |
| 4 | >100 | >100 | 6.2 |
| 5 | >100 | >100 | 6.2 |
| 6 | .05 | .05 | .78 |
| 7 | 100 | 100 | >100 |
| 8 | 6.2 | 6.2 | 50 |
| 9 | >100 | >100 | >100 |
| 10 | >100 | >100 | >100 |
| 11 | 50 | 50 | >100 |
| 12 | 25 | 50 | >100 |
| 13 | 25 | 100 | >100 |
| 14 | >100 | >100 | >100 |
| 15 | >100 | >100 | >100 |

| II | A | B | P |
|---|---|---|---|
| 4 | .05 | .01 | 25 |
| 6 | >100 | >100 | >100 |
| 5 | >100 | >100 | >100 |
| 16 | .78 | 1.56 | 12.5 |

| III | A | | P |
|---|---|---|---|
| 1 | >100 | | 6.2 |
| 2 | >100 | | 6.2 |
| 3 | .20 | | .78 |

| IV-1 | A | | P |
|---|---|---|---|
| 1 | >100 | | 12.5 |
| 2 | >100 | | >100 |

| IV-2 | A | | P |
|---|---|---|---|
| 1 | >100 | | 12.5 |
| 2 | >100 | | 12.5 |
| 3 | >100 | | 12.5 |
| 4 | >100 | | 12.5 |
| 5 | >100 | | 12.5 |

TABLE II

EXAMPLE II

| I | A | B | P |
|---|---|---|---|
| 1 | .20 | .39 | 1.56 |
| 2 | .20 | .20 | 1.56 |
| 3 | >100 | >100 | >100 |
| 4 | >100 | >100 | 6.2 |
| 5 | >100 | >100 | 6.2 |
| 6 | .05 | .05 | .70 |
| 7 | 50 | >100 | >100 |
| 8 | 6.2 | 3.1 | >100 |
| 9 | >100 | >100 | >100 |
| 10 | >100 | >100 | >100 |
| 11 | 50 | 50 | >100 |
| 12 | 25 | 25 | >100 |
| 13 | 50 | 50 | >100 |
| 14 | >100 | >100 | >100 |
| 15 | >100 | >100 | >100 |

| II | A | B | P |
|---|---|---|---|
| 4 | .01 | .01 | 2.5 |
| 6 | >100 | >100 | >100 |
| 5 | >100 | >100 | 25 |
| 16 | 1.56 | 3.1 | >100 |

| III | A | | P |
|---|---|---|---|
| 1 | >100 | | 6.2 |
| 2 | >100 | | 6.2 |
| 3 | .10 | | 1.56 |

| IV-1 | A | | P |
|---|---|---|---|
| 1 | >100 | | 12.5 |
| 2 | >100 | | >100 |

| IV-2 | A | | P |
|---|---|---|---|
| 1 | >100 | | 6.2 |
| 2 | >100 | | 6.2 |
| 3 | >100 | | 6.2 |
| 4 | >100 | | 6.2 |
| 5 | >100 | | 6.2 |

TABLE III
EXAMPLE V

| INFECTION | LD$_{50}$ | ROUTE OF MEDICATION | DOSAGE LEVELS | | | | | cd$_{50}$ |
|---|---|---|---|---|---|---|---|---|
| S.aureus (Smith) | 10-100 Rt-IP | Oral | 300 80 | 150 20 | 75 0 | 37.5 0 | 18.75 0 | 150 300 |

TABLE IV
EXAMPLE V

| I | A | B | P |
|---|---|---|---|
| 1 | .20 | .20 | .39 |
| 2 | .20 | .20 | .20 |
| 3 | >100 | >100 | >100 |
| 4 | >100 | >100 | 1.56 |
| 5 | >100 | >100 | 1.56 |
| 6 | .05 | .05 | .10 |
| 7 | 50 | 100 | >100 |
| 8 | 3.1 | 6.2 | 25 |
| 9 | >100 | >100 | >100 |
| 10 | >100 | >100 | >100 |
| 11 | 50 | 100 | 6.2 |
| 12 | 12.5 | 25 | 50 |
| 13 | 50 | 50 | >100 |
| 14 | >100 | >100 | >100 |
| 15 | >100 | >100 | >100 |
| II | A | B | P |
| 4 | .05 | .10 | .02 |
| 6 | >100 | >100 | >100 |
| 5 | >100 | >100 | >100 |
| 16 | 1.56 | 3.1 | 25 |
| III | A | | P |
| 1 | >100 | | .78 |
| 2 | >100 | | .78 |
| 3 | .10 | | .39 |
| IV-1 | A | | P |
| 1 | >100 | | >100 |
| 2 | >100 | | .78 |
| IV-2 | A | | P |
| 1 | >100 | | .78 |
| 2 | >100 | | .78 |
| 3 | >100 | | .78 |
| 4 | >100 | | .78 |
| 5 | >100 | | .78 |

TABLE V
EXAMPLE VI

| INFECTION | LD$_{50}$ | ROUTE OF MEDICATION | DOSAGE LEVELS | | | | | CD$_{50}$ |
|---|---|---|---|---|---|---|---|---|
| S.aureus (Smith) | 10-100 Rt-IP | Oral | 300 50 | 150 10 | 75 20 | 37.5 20 | 18.75 10 | 150 300 |

TABLE VI
EXAMPLE VI

| I | A | B | P |
|---|---|---|---|
| 1 | .20 | .39 | .20 |
| 2 | .20 | .39 | .20 |
| 3 | >100 | >100 | >100 |
| 4 | >100 | >100 | .78 |
| 5 | >100 | >100 | .78 |
| 6 | .05 | .05 | .05 |
| 7 | 50 | 100 | >100 |
| 8 | 3.1 | 3.1 | 25 |
| 9 | >100 | >100 | >100 |
| 10 | >100 | >100 | >100 |
| 11 | 25 | 100 | 6.2 |
| 12 | 25 | 25 | 25 |
| 13 | 50 | 100 | >100 |
| 14 | >100 | >100 | 100 |
| 15 | >100 | >100 | 100 |
| II | A | B | P |
| 4 | .02 | .02 | .25 |
| 6 | >100 | >100 | >100 |
| 5 | >100 | >100 | >100 |
| 16 | 3.1 | 6.2 | 50 |
| III | A | B | P |
| 1 | >100 | | .78 |
| 2 | >100 | | .78 |
| 3 | .20 | | .20 |
| IV-1 | A | B | P |
| 1 | >100 | | 1.56 |
| 2 | >100 | | >100 |
| IV-2 | A | B | P |
| 1 | >100 | | .78 |
| 2 | >100 | | .78 |
| 3 | >10C | | .78 |
| 4 | >100 | | .78 |
| 5 | >100 | | .78 |

TABLE VII
EXAMPLE VII

| I | A | B | P |
|---|---|---|---|
| 1 | .39 | .39 | .78 |
| 2 | .20 | .39 | .78 |
| 3 | >100 | >100 | >100 |
| 4 | >100 | >100 | .78 |
| 5 | >100 | >100 | .78 |
| 6 | .05 | .05 | .39 |
| 7 | 100 | 100 | >100 |
| 8 | 6.2 | 6.2 | 100 |
| 9 | >100 | >100 | >100 |
| 10 | >100 | >100 | >100 |
| 11 | 50 | 50 | >100 |
| 12 | 25 | 50 | >100 |
| 13 | 25 | 100 | >100 |
| 14 | >100 | >100 | >100 |
| 15 | >100 | >100 | >100 |
| II | A | B | P |
| 4 | .05 | .01 | 2.5 |
| 6 | >100 | >100 | >100 |
| 5 | >100 | >100 | >100 |
| 16 | .78 | 1.56 | 12.5 |
| III | A | B | P |
| 1 | >100 | | .78 |
| 2 | >100 | | .78 |
| 3 | .20 | | .20 |
| IV-1 | A | B | P |
| 1 | >100 | | 3.1 |
| 2 | >100 | >100 | |
| IV-2 | A | B | P |
| 1 | >100 | | 1.56 |
| 2 | >100 | | 3.1 |
| 3 | >100 | | 1.56 |
| 4 | >100 | | 1.56 |
| 5 | >100 | | 1.56 |

TABLE VIII
EXAMPLE VIII

| I | A | B | P |
|---|---|---|---|
| 1 | .20 | | .39 |
| 2 | .20 | | .39 |
| 3 | >100 | | >100 |
| 4 | >100 | | 3.1 |
| 5 | >100 | | 3.1 |
| 6 | .05 | | .10 |
| 7 | 50 | | >100 |
| 8 | 6.2 | | 25 |
| 9 | >100 | | >100 |
| 10 | >100 | | >100 |
| 11 | 50 | | >100 |
| 12 | 25 | | 100 |
| 13 | 50 | | >100 |
| 14 | >100 | | >100 |
| 15 | >100 | | >100 |

| II | A | B | P |
|---|---|---|---|
| 4 | .02 | | .02 |
| 6 | >100 | | >100 |
| 5 | >100 | | >100 |
| 16 | 3.1 | | 50 |

| III | A | B | P |
|---|---|---|---|
| 1 | >100 | | .78 |
| 2 | >100 | | .78 |
| 3 | .10 | | .39 |

| IV-1 | A | B | P |
|---|---|---|---|
| 1 | >100 | | 1.56 |
| 2 | >100 | | >100 |

| IV-2 | A | B | P |
|---|---|---|---|
| 1 | >100 | | .78 |
| 2 | >100 | | .78 |
| 3 | >100 | | .78 |
| 4 | >100 | | .78 |
| 5 | >100 | | .78 |

TABLE IX
EXAMPLE IX

| I | A | B | P |
|---|---|---|---|
| 1 | .20 | | .39 |
| 2 | .20 | | .39 |
| 3 | >100 | | 100 |
| 4 | >100 | | .78 |
| 5 | >100 | | .78 |
| 6 | .05 | | .20 |
| 7 | 50 | | >100 |
| 8 | 6.2 | | >100 |
| 9 | >100 | | >100 |
| 10 | >100 | | >100 |
| 11 | 50 | | >100 |
| 12 | 25 | | >100 |
| 13 | 50 | | >100 |
| 14 | >100 | | 50 |
| 15 | >100 | | 50 |

| II | A | B | P |
|---|---|---|---|
| 4 | .02 | | .25 |
| 6 | >100 | | >100 |
| 5 | >100 | | 50 |
| 16 | 3.1 | | >100 |

| III | A | B | P |
|---|---|---|---|
| 1 | >100 | | .78 |
| 2 | >100 | | .78 |
| 3 | .10 | | .20 |

| IV-1 | A | B | P |
|---|---|---|---|
| 1 | >100 | | .75 |
| 2 | >100 | | 25 |

| IV-2 | A | B | P |
|---|---|---|---|
| 1 | >100 | | .39 |
| 2 | >100 | | .39 |
| 3 | >100 | | .78 |
| 4 | >100 | | .39 |
| 5 | >100 | | .39 |

TABLE X
EXAMPLE X

| I | A | B | P |
|---|---|---|---|
| 1 | .20 | | .78 |
| 2 | .20 | | .78 |
| 3 | >100 | | >100 |
| 4 | >100 | | 1.56 |
| 5 | >100 | | 1.56 |
| 6 | .05 | | .20 |
| 7 | 50 | | >100 |
| 8 | 6.2 | | >100 |
| 9 | >100 | | >100 |
| 10 | >100 | | >100 |
| 11 | 50 | | >100 |
| 12 | 25 | | >100 |
| 13 | 50 | | >100 |
| 14 | >100 | | >100 |
| 15 | >100 | | >100 |

| II | A | B | P |
|---|---|---|---|
| 4 | .02 | | .25 |
| 6 | >100 | | >100 |
| 5 | >100 | | >100 |
| 16 | 3.1 | | >100 |

| III | A | B | P |
|---|---|---|---|
| 1 | >100 | | 1.56 |
| 2 | >100 | | 1.56 |
| 3 | .10 | | .39 |

| IV-1 | A | B | P |
|---|---|---|---|
| 1 | >100 | | .78 |
| 2 | >100 | | >100 |

| IV-2 | A | B | P |
|---|---|---|---|
| 1 | >100 | | .39 |
| 2 | >100 | | .78 |
| 3 | >100 | | .78 |
| 4 | >100 | | .78 |
| 5 | >100 | | .78 |

TABLE XI
EXAMPLE XI

| I | A | B | P |
|---|---|---|---|
| 1 | .20 | .20 | .78 |
| 2 | .20 | .20 | .78 |
| 3 | >100 | >100 | >100 |
| 4 | >100 | >100 | 3.1 |
| 5 | >100 | >100 | 3.1 |
| 6 | .05 | .05 | .39 |
| 7 | 50 | 100 | >100 |
| 8 | 6.2 | 6.2 | 25 |
| 9 | >100 | >100 | >100 |
| 10 | >100 | >100 | >100 |
| 11 | 50 | 50 | >100 |
| 12 | 25 | 25 | >100 |
| 13 | 50 | 50 | 100 |
| 14 | >100 | >100 | >100 |
| 15 | >100 | >100 | >100 |

| II | A | B | P |
|---|---|---|---|
| 4 | .05 | .01 | .02 |
| 6 | >100 | >100 | >100 |
| 5 | >100 | >100 | >100 |
| 16 | 1.56 | 3.1 | 50 |

| III | A | B | P |
|---|---|---|---|
| 1 | >100 | | 3.1 |
| 2 | >100 | | 3.1 |
| 3 | .10 | | .78 |

| IV-1 | A | P |
|---|---|---|
| 1 | >100 | 6.2 |
| 2 | >100 | >100 |

| IV-2 | A | P |
|---|---|---|
| 1 | >100 | 3.1 |
| 2 | >100 | 6.2 |
| 3 | >100 | 6.2 |
| 4 | >100 | 3.1 |
| 5 | >100 | 6.2 |

TABLE XII
EXAMPLE XII

| INFECTION | LD$_{50}$ | ROUTE OF MEDICATION | DOSAGE LEVELS | | | | | CD$_{50}$ |
|---|---|---|---|---|---|---|---|---|
| S.aureus (Smith) | 10–100 Rt.IP | Oral | 300 30 | 150 0 | 75 0 | 37.5 0 | 18.75 20 | >300 |

TABLE XIII
EXAMPLE XII

| I | A | B | P |
|---|---|---|---|
| 1 | .20 | .39 | .39 |
| 2 | .20 | .39 | .39 |
| 3 | >100 | >100 | >100 |
| 4 | >100 | >100 | .78 |
| 5 | >100 | >100 | .78 |
| 6 | .05 | .05 | .10 |
| 7 | 50 | 100 | 100 |
| 8 | 3.1 | 3.1 | 12.5 |
| 9 | >100 | >100 | >100 |
| 10 | >100 | >100 | >100 |
| 11 | 25 | 100 | 12.5 |
| 12 | 25 | 25 | 25 |
| 13 | 50 | 100 | >100 |
| 14 | >100 | >100 | >100 |
| 15 | >100 | >100 | >100 |

| II | A | B | P |
|---|---|---|---|
| 4 | .02 | .02 | .02 |
| 6 | >100 | >100 | >100 |
| 5 | >100 | >100 | 25 |
| 16 | 3.1 | 6.2 | 12.5 |

| III | A | B | P |
|---|---|---|---|
| 1 | >100 | | .78 |
| 2 | >100 | | .78 |
| 3 | .20 | | .20 |

| IV-1 | A | B | P |
|---|---|---|---|
| 1 | >100 | | 1.56 |
| 2 | >100 | | >100 |

| IV-2 | A | B | P |
|---|---|---|---|
| 1 | >100 | | .78 |
| 2 | >100 | | 1.56 |
| 3 | >100 | | 1.56 |
| 4 | >100 | | 3.1 |
| 5 | >100 | | .78 |

TABLE XIV
EXAMPLE XVIII

| I | A | B | P |
|---|---|---|---|
| 1 | .20 | .39 | .78 |
| 2 | .10 | .20 | .78 |
| 3 | >100 | >100 | >100 |
| 4 | >100 | >100 | 3.1 |
| 5 | >100 | >100 | 3.1 |
| 6 | .05 | .05 | .20 |
| 7 | 50 | 100 | >100 |
| 8 | 3.1 | 3.1 | 25 |
| 9 | >100 | >100 | >100 |
| 10 | >100 | >100 | >100 |
| 11 | 25 | 50 | >100 |
| 12 | 25 | 50 | >100 |
| 13 | 50 | 100 | >100 |
| 14 | >100 | >100 | >100 |
| 15 | >100 | >100 | >100 |

| II | A | B | P |
|---|---|---|---|
| 4 | .01 | .01 | .02 |
| 6 | >100 | >100 | >100 |
| 5 | >100 | >100 | 100 |
| 16 | 6.2 | 6.2 | 6.2 |

TABLE XIV-continued
EXAMPLE XVIII

| III | A | B | P |
|---|---|---|---|
| 1 | >100 | | 1.56 |
| 2 | >100 | | 1.56 |
| 3 | .20 | | .78 |

| IV-1 | A | B | P |
|---|---|---|---|
| 1 | >100 | | 3.1 |
| 2 | >100 | | >100 |

| IV-11 | A | | P |
|---|---|---|---|
| 1 | >100 | | 3.1 |
| 2 | >100 | | 3.1 |
| 3 | >100 | | 3.1 |
| 4 | >100 | | 3.1 |
| 5 | >100 | | 3.1 |

TABLE XV
EXAMPLE XIV

| I | A | B | P |
|---|---|---|---|
| 1 | .20 | .39 | 1.56 |
| 2 | .20 | .20 | 1.56 |
| 3 | >100 | >100 | >100 |
| 4 | >100 | >100 | 3.1 |
| 5 | >100 | >100 | 3.1 |
| 6 | .05 | .05 | 1.56 |
| 7 | 50 | 100 | >100 |
| 8 | 6.2 | 3.1 | >100 |
| 9 | >100 | >100 | >100 |
| 10 | >100 | >100 | >100 |
| 11 | 50 | 50 | >100 |
| 12 | 25 | 25 | >100 |
| 13 | 50 | 50 | >100 |
| 14 | >100 | >100 | >100 |
| 15 | >100 | >100 | >100 |

| II | A | B | P |
|---|---|---|---|
| 4 | .01 | .01 | .02 |
| 6 | >100 | >100 | >100 |
| 5 | >100 | >100 | >100 |
| 16 | 1.56 | 3.1 | >100 |

| III | A | B | P |
|---|---|---|---|
| 1 | >100 | | 6.2 |
| 2 | >100 | | 6.2 |
| 3 | .10 | | 1.56 |

| IV-1 | A | B | P |
|---|---|---|---|
| 1 | >100 | | 3.1 |
| 2 | >100 | | >100 |

| IV-2 | A | B | P |
|---|---|---|---|
| 1 | >100 | | 3.1 |
| 2 | >100 | | 3.1 |
| 3 | >100 | | 3.1 |
| 4 | >100 | | 1.56 |
| 5 | >100 | | 3.1 |

TABLE XVI
EXAMPLE XV

| Infection | LD$_{50}$ | ROUTE OF MEDICATION | DOSAGE LEVELS | | | | | CD$_{50}$ |
|---|---|---|---|---|---|---|---|---|
| S.aureus (Smith) Rt-IP | 10–100 | Oral | 300 60 | 150 0 | 75 0 | 37.5 10 | 18.75 10 | 150 300 |

TABLE XVII

EXAMPLE XV

| I | A | B | P |
|---|---|---|---|
| 1 | .20 | .20 | .20 |
| 2 | .20 | .20 | .20 |
| 3 | >100 | >100 | >100 |
| 4 | >100 | >100 | .39 |
| 5 | >100 | >100 | .78 |
| 6 | .05 | .05 | .10 |
| 7 | 25 | 50 | >100 |
| 8 | 6.2 | 6.2 | 25 |
| 9 | >100 | >100 | >100 |
| 10 | >100 | >100 | >100 |
| 11 | 50 | 50 | >100 |
| 12 | 12.5 | 25 | >100 |
| 13 | 25 | 50 | >100 |
| 14 | >100 | >100 | >100 |
| 15 | >100 | >100 | >100 |

| II | A | B | P |
|---|---|---|---|
| 4 | .05 | .10 | .05 |
| 6 | >100 | >100 | >100 |
| 5 | >100 | >100 | >100 |
| 16 | 1.56 | 3.1 | 50 |

| III | A | B | P |
|---|---|---|---|
| 1 | >100 | | .78 |
| 2 | >100 | | .78 |
| 3 | .10 | | .20 |

| IV-I | A | B | P |
|---|---|---|---|
| 1 | >100 | | .78 |
| 2 | >100 | | >100 |

| IV-II | A | B | P |
|---|---|---|---|
| 1 | >100 | | .78 |
| 2 | >100 | | .78 |
| 3 | >100 | | .78 |
| 4 | >100 | | .78 |
| 5 | >100 | | .78 |

TABLE XVIII

EXAMPLE XVI

| I | A | B | P |
|---|---|---|---|
| 1 | .20 | .39 | .78 |
| 2 | .20 | .20 | .78 |
| 3 | >100 | >100 | >100 |
| 4 | >100 | >100 | 3.1 |
| 5 | >100 | >100 | 6.2 |
| 6 | .05 | .50 | .78 |
| 7 | 50 | 100 | >100 |
| 8 | 6.2 | 6.2 | 25 |
| 9 | >100 | >100 | >100 |
| 10 | >100 | >100 | >100 |
| 11 | 50 | 50 | 25 |
| 12 | 25 | 25 | 50 |
| 13 | 50 | 50 | >100 |
| 14 | >100 | >100 | >100 |
| 15 | >100 | >100 | >100 |

| II | A | B | P |
|---|---|---|---|
| 4 | .01 | .01 | .05 |
| 6 | >100 | >100 | >100 |
| 5 | >100 | >100 | >100 |
| 16 | 1.56 | 3.1 | 25 |

| III | A | B | P |
|---|---|---|---|
| 1 | >100 | | 12.5 |
| 2 | >100 | | 6.2 |
| 3 | 10 | | .78 |

| IV-I | A | B | P |
|---|---|---|---|
| 1 | >100 | | 6.2 |
| 2 | >100 | | >100 |

| IV-II | A | B | P |
|---|---|---|---|
| 1 | >100 | | 3.1 |
| 2 | >100 | | 6.2 |
| 3 | >100 | | 6.2 |
| 4 | >100 | | 6.2 |
| 5 | >100 | | 3.1 |

TABLE XIX

EXAMPLE XVII

| INFECTION | LD$_{50}$ | ROUTE OF MEDICATION | DOSAGE LEVELS | | | | | CD$_{50}$ |
|---|---|---|---|---|---|---|---|---|
| S.aureus (Smith) | 10-100 Rt-IP | Oral | 300 80 | 150 0 | 75 10 | 37.5 10 | 18.75 0 | 150 300 |

TABLE XX

EXAMPLE XVII

| I | A | B | P |
|---|---|---|---|
| 1 | .20 | .39 | 100 |
| 2 | .20 | .39 | 100 |
| 3 | >100 | >100 | >100 |
| 4 | >100 | >100 | >100 |
| 5 | >100 | >100 | >100 |
| 6 | .05 | .05 | 25 |
| 7 | 50 | 100 | >100 |
| 8 | 3.1 | 3.1 | >100 |
| 9 | >100 | >100 | >100 |
| 10 | >100 | >100 | >100 |
| 11 | 25 | 100 | >100 |
| 12 | 25 | 25 | >100 |
| 13 | 50 | 100 | >100 |
| 14 | >100 | >100 | >100 |
| 15 | >100 | >100 | >100 |

| II | A | B | P |
|---|---|---|---|
| 4 | .02 | .02 | 5.0 |
| 6 | >100 | >100 | >100 |
| 5 | >100 | >100 | >100 |
| 16 | 3.1 | 6.2 | >100 |

TABLE XXI

EXAMPLE XIX

| I | A | B | P |
|---|---|---|---|
| 1 | .39 | .39 | .78 |
| 2 | .20 | .39 | .39 |
| 3 | >100 | >100 | >100 |
| 4 | >100 | >100 | .78 |
| 5 | >100 | >100 | 1.56 |
| 6 | .05 | .05 | .20 |
| 7 | 100 | 100 | >100 |
| 8 | 6.2 | 6.2 | 12.5 |
| 9 | >100 | >100 | >100 |
| 10 | >100 | >100 | >100 |
| 11 | 50 | 50 | >100 |
| 12 | 25 | 50 | >100 |
| 13 | 50 | 100 | >100 |
| 14 | >100 | >100 | >100 |
| 15 | >100 | >100 | >100 |

| II | A | B | P |
|---|---|---|---|
| 4 | .05 | .01 | .25 |
| 6 | >100 | >100 | >100 |
| 5 | >100 | >100 | 100 |
| 16 | .78 | 1.56 | 6.2 |

| III | A | B | P |
|---|---|---|---|
| 1 | >100 | | 1.56 |
| 2 | >100 | | 1.56 |
| 3 | .20 | | .78 |

| IV-I | A | B | P |
|---|---|---|---|
| 1 | >100 | | 3.1 |
| 2 | >100 | | >100 |

| IV-II | A | B | P |
|---|---|---|---|
| 1 | >100 | | 1.56 |
| 2 | >100 | | 1.56 |
| 3 | >100 | | 1.56 |
| 4 | >100 | | 1.56 |
| 5 | >100 | | 1.56 |

TABLE XVIII-continued

EXAMPLE XVI

| 1 | >100 | 3.1 |
| 2 | >100 | 6.2 |
| 3 | >100 | 6.2 |
| 4 | >100 | 6.2 |
| 5 | >100 | 3.1 |

TABLE XXII

EXAMPLE XX

| I | A | B | P |
|---|---|---|---|
| 1 | .39 | .39 | 6.2 |
| 2 | .39 | .39 | 6.2 |
| 3 | >100 | >100 | >100 |
| 4 | >100 | >100 | 25 |
| 5 | >100 | >100 | 25 |
| 6 | .05 | .05 | 3.1 |
| 7 | 100 | 100 | >100 |
| 8 | 6.2 | 6.2 | >100 |
| 9 | >100 | >100 | >100 |
| 10 | >100 | >100 | >100 |
| 11 | 50 | 50 | >100 |
| 12 | 25 | 50 | >100 |
| 13 | 50 | 100 | >100 |
| 14 | >100 | >100 | >100 |
| 15 | >100 | >100 | >100 |

| II | A | B | P |
|---|---|---|---|
| 4 | .02 | .02 | .25 |
| 6 | >100 | >100 | >100 |
| 5 | >100 | >100 | >100 |
| 16 | 3.1 | 6.2 | >100 |

TABLE XXIII

EXAMPLE XXI

| I | A | B | P |
|---|---|---|---|
| 1 | .39 | .39 | >100 |
| 2 | .39 | .39 | >100 |
| 3 | >100 | >100 | >100 |
| 4 | >100 | >100 | >100 |
| 5 | >100 | >100 | >100 |
| 6 | .05 | .05 | 25 |
| 7 | 100 | 100 | >100 |
| 8 | 6.2 | 6.2 | >100 |
| 9 | >100 | >100 | >100 |
| 10 | >100 | >100 | >100 |
| 11 | 50 | 50 | >100 |
| 12 | 25 | 50 | >100 |
| 13 | 50 | 100 | >100 |
| 14 | >100 | >100 | >100 |
| 15 | >100 | >100 | >100 |

| II | A | B | P |
|---|---|---|---|
| 4 | .02 | .02 | 1.0 |
| 6 | >100 | >100 | >100 |
| 5 | >100 | >100 | >100 |
| 16 | 3.1 | 6.2 | >100 |

TABLE XXIV

EXAMPLE XXII

| I | A | B | P |
|---|---|---|---|
| 1 | .20 | .39 | 12.5 |
| 2 | .10 | .20 | 12.5 |
| 3 | >100 | >100 | >100 |
| 4 | >100 | >100 | >100 |
| 5 | >100 | >100 | >100 |
| 6 | .05 | .05 | 6.2 |
| 7 | 50 | 100 | >100 |
| 8 | 3.1 | 3.1 | >100 |
| 9 | >100 | >100 | >100 |
| 10 | >100 | >100 | >100 |
| 11 | 25 | 50 | >100 |
| 12 | 25 | 50 | >100 |
| 13 | 50 | 100 | >100 |
| 14 | >100 | >100 | >100 |
| 15 | >100 | >100 | >100 |

| II | A | B | P |
|---|---|---|---|
| 4 | .01 | .01 | .50 |
| 6 | >100 | >100 | >100 |
| 5 | >100 | >100 | >100 |
| 16 | 6.2 | 6.2 | >100 |

The compounds of the invention here are useful as antibiotics when administered to warm-blooded animals at a preferred dosage of 25-2000 mg./kg. of body weight daily to treat infections in which one of the above or another susceptible bacterial organism is the causative agent. More often the dosage is 75-1000 mg./kg.

Although administration is possible by the intraperitoneal route wherein the dose is dissolved or suspended in an inert physiologically harmless agent such as aqueous tragacanth, the preferred route is oral, either in capsule or tablet form. Capsules can, in addition to the active erythromycin also contain inert fillers such as lactose.

Tablets are made in the usual manner on tableting presses, and although the active compounds may be tableted alone, it is preferred that a release agent such as magnesium stearate to aid in freeing the tablets from the machine dies during manufacture, together with a binder such as starch to assure good particle cohesion are included in a blend of active ingredient and diluents prior to tableting. After tableting, the tablets can be coated if desired. A preferred blend for tableting is as follows:

|  | Percent |
|---|---|
| Erythromycin Compound | 77 |
| Magnesium stearate | 2 |
| Starch powder | 21 |

We claim:

1. A 4″-O-sulfonyl erythromycin derivative of the following structural formula:

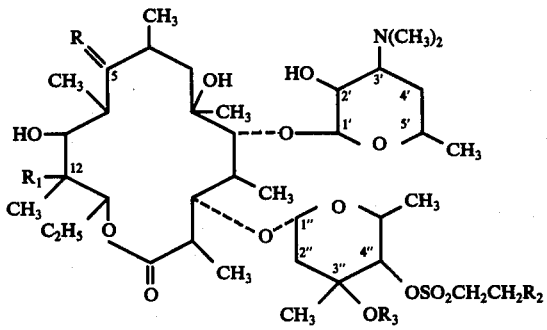

wherein R is methyloxime, $R_1$ is hydrogen or hydroxy and $R_2$ is, phthalimido, alkanoylamido, nitro- or amino-substituted-benzoylamido or -benzenesulfamido, phenyl-ureido or -thioureido wherein said phenyl group may carry dimethylamino, methoxy, chloro or nitro, or CBZ-glycylamido and $R_3$ is hydrogen or methyl.

2. A compound according to claim 1 wherein $R_1$ and $R_3$ are hydrogen and $R_2$ is phthalimido.

3. A compound according to claim 1 where $R_1$ is hydrogen, $R_3$ is methyl and $R_2$ is a substituted phenylthiourea.

4. A compound according to claim 1 wherein $R_1$ is hydroxy, $R_3$ is methyl and $R_2$ is a substituted phenylthiourea.

5. A compound according to claim 1 wherein $R_1$ is hydrogen, $R_3$ is methyl and $R_2$ is a substituted phenylurea.

6. A compound according to claim 1 wherein R is methyloxime, $R_1$ is hydroxy, $R_3$ is methyl and $R_2$ is a substituted phenylurea.

* * * * *